(12) United States Patent
Taffler

(10) Patent No.: US 11,914,080 B2
(45) Date of Patent: *Feb. 27, 2024

(54) HIGH SPEED DISTRIBUTION OF DATA FOR CONTROL OF ULTRASOUND DEVICES

(71) Applicant: ACOUSTIIC INC., Pacific Palisades, CA (US)

(72) Inventor: Sean Taffler, Pacific Palisades, CA (US)

(73) Assignee: Acoustiic Inc., Pacific palisades, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/112,563

(22) Filed: Feb. 22, 2023

(65) Prior Publication Data
US 2023/0228859 A1 Jul. 20, 2023

Related U.S. Application Data

(63) Continuation of application No. 17/209,136, filed on Mar. 22, 2021, now Pat. No. 11,592,541, which is a (Continued)

(51) Int. Cl.
*G01S 7/52* (2006.01)
*G01S 15/89* (2006.01)
(Continued)

(52) U.S. Cl.
CPC ...... *G01S 7/52087* (2013.01); *G01S 15/8915* (2013.01); *H04B 10/25891* (2020.05); *H04B 10/40* (2013.01)

(58) Field of Classification Search
CPC ............. G01S 7/52087; G01S 15/8915; H04B 10/25891; H04B 10/40
See application file for complete search history.

(56) References Cited

U.S. PATENT DOCUMENTS 6,126,602 A 10/2000 Savord
10,955,537 B2 3/2021 Taffler
(Continued)

FOREIGN PATENT DOCUMENTS

DE 19530150 A1 2/1997
EP 3836840 A1 * 6/2021 ............... A61B 8/56
(Continued)

OTHER PUBLICATIONS

International Search Report and Written Opinion for Application No. PCT/US2019/046913, dated Nov. 29, 2019, 11 pages.
(Continued)

*Primary Examiner* — Daniel Pihulic
(74) *Attorney, Agent, or Firm* — Ian Harrison; Butzel Long

(57) ABSTRACT

A method of distributing data to a transducer array of an ultrasonic device, the transducer array including transduction elements arranged in module units, includes generating a data packet using an optical transceiver controlled by a controller, the data packet including activation instructions encoded in a first wavelength, transmitting the data packet from the controller to a target device via a signal in an optical fiber, the target device having a beam divider device, splitting the data signal, using the beam divider device, into a plurality of data streams, where each of the data streams carries the data packet in an identical phase, transmitting the data streams to the module units, and activating the transduction elements based on the received data streams.

12 Claims, 3 Drawing Sheets

Related U.S. Application Data continuation of application No. 16/104,800, filed on Aug. 17, 2018, now Pat. No. 10,955,537.

(51) Int. Cl.
  *H04B 10/40* (2013.01)
  *H04B 10/25* (2013.01)

(56) References Cited

U.S. PATENT DOCUMENTS

| | | | |
|---|---|---|---|
| 11,592,541 B2 * | 2/2023 | Taffler | A61B 8/56 |
| 2002/0054409 A1 | 5/2002 | Bartur | |
| 2013/0226002 A1 | 8/2013 | Miyachi | |
| 2018/0058845 A1 | 3/2018 | Arai | |
| 2020/0057153 A1 * | 2/2020 | Taffler | H04B 10/40 |
| 2021/0208264 A1 * | 7/2021 | Taffler | H04B 10/25891 |
| 2023/0249220 A1 * | 8/2023 | Taffler | B06B 1/0215 367/137 |

FOREIGN PATENT DOCUMENTS

| | | | | |
|---|---|---|---|---|
| EP | 3836840 B1 * | 8/2023 | | A61B 8/4477 |
| EP | 4250598 A2 * | 9/2023 | | A61B 8/4477 |
| WO | 2020037263 A1 | 2/2020 | | |
| WO | WO-2020037263 A1 * | 2/2020 | | A61B 8/56 |

OTHER PUBLICATIONS

International Preliminary Report on Patentability for App. No. PCT/US2019/046913, dated Mar. 4, 2021, 7 pages.
European Patent Office Communication pursuant to Rules 161(1) and 162 EPC for App. No. EP19762061.0, dated Mar. 26, 2021, 3 pages.

* cited by examiner

HIGH SPEED DISTRIBUTION OF DATA FOR CONTROL OF ULTRASOUND DEVICES

BACKGROUND

In typical imaging and therapy devices there are multiple individual transducers, sub arrays, or elements. Individual transducers can be turned on or off at different times. When many transducers are operated at the same time (as is typical with HIFU or imaging) the amount of data that has to be transported to and from the transducers is significant and high speed transportation methods need to be used to distribute the data. Typically, data distribution methods rely on utilizing copper or other conductors to transmit data.

In addition to the large amount of data that has to be delivered, strict timing requirements must be met, particularly when the frequency of operation is in the MHz region and there are IO's or more of phase steps. In such situations most conventional methods of data delivery are problematic. Multiple individual conductors can be used to deliver the data and synchronization pulses, however this can lead to an unwieldy cable bundle making use and operation of the device challenging.

BRIEF SUMMARY

According to an embodiment of the disclosed subject matter, a method of distributing data to a transducer array of an ultrasonic device, the transducer array including drivers to control groups of transduction elements arranged in modules, includes generating a data packet from an optical transceiver in a controller, the data packet including activation instructions encoded in a first wavelength, transmitting the data packet from the controller to a target device via a data signal in an optical fiber, the target device having a beam divider device, splitting the data signal, using the beam divider device, into a plurality of data streams, with each of the data streams carrying the data packet in an identical phase, transmitting the data streams to the drivers, and activating the transduction elements based on the received data streams.

According to another embodiment of the disclosed subject matter, an ultrasonic system includes a controller having a memory, an optical transceiver, and a processor that controls the optical transceiver to generate a data packet that includes activation instructions encoded in a first wavelength, and a target device comprising an transducer array and a beam divider device connected to the optical transceiver by an optical fiber, the transducer array having drivers that control transduction elements of the transducer array. The controller transmits a data packet to the target device in a data signal via the optical fiber, the beam divider device splits the data signal into a plurality of data streams and transmits the data streams to the drivers, and the drivers activate the transduction elements based on the received data streams.

Additional features, advantages, and embodiments of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Figure 1:
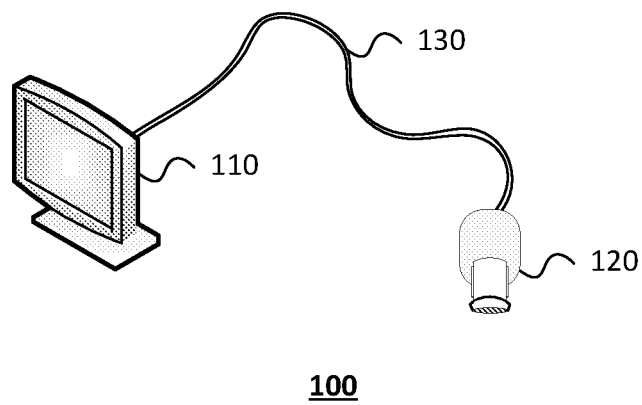
FIG. 1 shows a high speed data distribution ultrasound system according to an embodiment of the disclosed subject matter.

Various aspects or features of this disclosure are described with reference to the drawings, wherein like reference numerals are used to refer to like elements throughout. In this specification, numerous details are set forth in order to provide a thorough understanding of this disclosure. It should be understood, however, that certain aspects of disclosure may be practiced without these specific details, or with other methods, components, materials, etc. In other instances, well-known structures and devices are shown in block diagram form to facilitate describing the subject disclosure.

While, for purposes of simplicity of explanation, the methodologies are shown and described as a series of operations within the context of various flowcharts, it is to be understood and appreciated that in embodiments of the disclosure some operations may occur in different orders and/or concurrently with other operations from that shown and described herein.

Moreover, not all illustrated operations may be required to implement a methodology in accordance with the disclosed subject matter.

Devices and methods are disclosed for instruction, clock and synchronization data distribution to an ultrasonic transducer array device in a system that enables high speed operation with the device being operated at some distance from a controlling computer. The disclosed methods and systems yield improvements in speed, size, and control compared to conventional systems.

In operations of an ultrasonic applicator, such as those used in imaging or therapy treatments (e.g., Low Intensity Focused Ultrasound (LIFU) or High Intensity Focused Ultrasound (HIFU)), control information must be distributed to multiple transduction devices. Any difference in arrival time of signals, for example, due to variations in physical distance between the receiving device and the source, can cause malfunction.

Multiple signal lines may be used to improve signal arrival time. However, minimizing the number of signal lines is beneficial for reducing complexity, size, and cost in practical systems. Moreover, in use cases where the applicator is to be placed in a Magnetic Resonance Imaging system (MRI), most conductive elements must be kept below 15 cm in length. As such, the requirement to place the applicator in the MRI presents challenges to the distribution of high speed data to the devices. Thus, the need to distribute control information is challenging if it has to be done in pseudo real-time.

An ultrasonic imager or therapeutic device includes multiple individual transducers. Individual transducers can be activated at different times in accordance with a signal, such as continuous-wave (CW) at a chosen frequency, pulse wave (PW), chirps, Gaussian, uni-polar or bi-polar pulses, square waves with two or more levels, or a signal of arbitrary frequency content. Predictable and consistent arrival of such activation signals at the individual transduction elements is critical to the performance of the system. In the disclosed embodiments, a reduced complexity implementation to achieve consistent activation signals can include a single fiber activating a level shifter to drive a single element. Greater control and precision can be achieved by implementing a modular approach, where by some amount of digital control logic receives a datagram and activates multiple elements at the correct time, phase, or clock ticks+ phase when phase>360° for large arrays.

For example, in a CW system, transducers all operate at the same frequency, but the phases between transducers may be different. A phase difference as few as two phase steps, 0°/360° or 180° or more may be present depending on the application. The upper limit to the number of phases is normally determined by the cost and complexity of the system, but even in a hypothetically powerful system at some level the phase difference of any two nearby levels approaches or falls below the timing uncertainty such that further increase in the number of phases has no effect on performance. Thus, precision of information arrival time limits performance and accuracy of any ultrasonic transducer array system in this regard. In other implementations where low numbers of ultrasound pulses are sent out there may be a need to activate elements precisely some number of cycles after first-activated elements effectively phase shifts >360°

Generally, in these systems data needs to be passed from a controlling system (computer, microprocessor, FPGA, or ASIC) to target transducer drivers. The drivers may be simple level shifters that amplify incoming data to a level appropriate to drive a transducer, or they may be complex circuits that generate the target signal internally and then amplify that signal or cause the signal to be manifested in the transducer (e.g., PWM synthesis), or they may be further configured to generate signals for multiple elements.

Transducer drivers may also have low noise amplifiers and analog-to-digital converters (ADCs) that allow the transducer to convert incoming pressure waves to electrical signals suitable for signal processing and analysis. This data typically is transmitted back to the controlling system for further analysis, imaging, or feedback purposes. Limited numbers of signal conductors, or signal conductors with low bandwidth, may limit the quantity of data returned. Simpler implementations may simply amplify the signal and send it back to the controlling computer for digitization and analysis.

The disclosed system distributes control information and synchronization pulses to multiple transducer modules via a light guide, for example, implemented in the form of an optical fiber. The light guide can be designed to distribute the same data signal to all modules with no phase change in the signal. The light guide can conversely be used as an aggregator of data transmitted back from the modules, thus reducing the burden on the cable to the applicator.

FIG. 1 shows a high speed data distribution ultrasound system 100 according to the disclosed embodiments. A controller 110 (e.g., a computer) is connected to a target device 120 (e.g., an ultrasound probe) via an optical fiber 130. The controller 110 uses an optical signal to send instructions to the target device 120 through the optical fiber 130.

Figure 2:
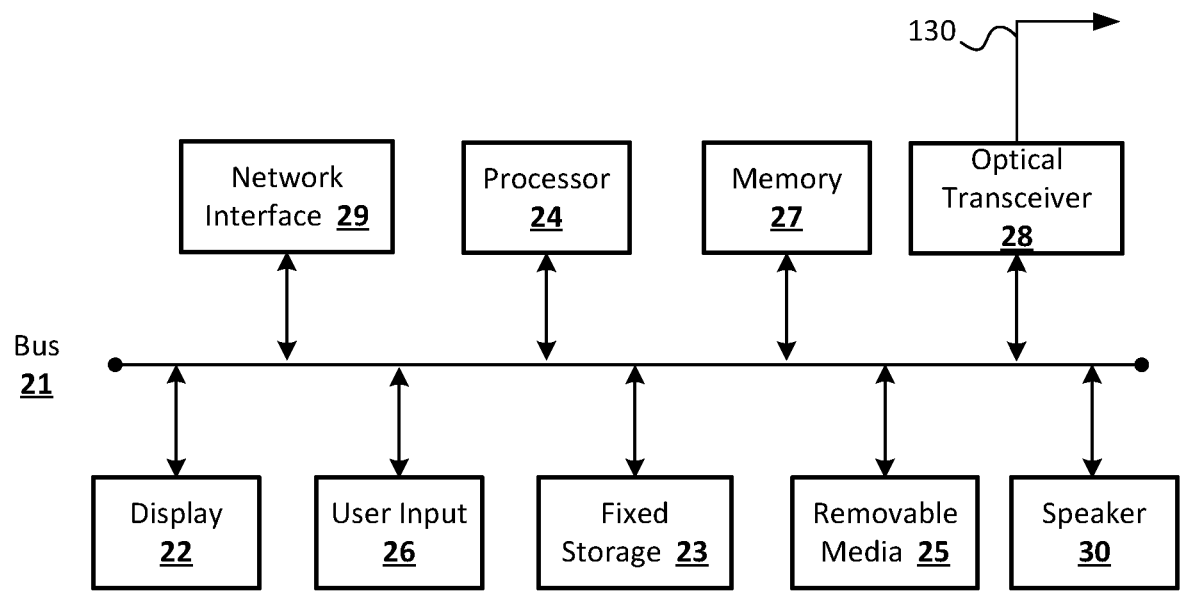
FIG. 2 shows a block diagram of a controller according to an embodiment of the disclosed subject matter.

FIG. 2 is a block diagram of an embodiment of the controller 110. The depicted embodiment includes a bus 21 that interconnects major components of the controller 110. Such components may include a central processor 24; a memory 27, such as Random Access Memory (RAM), Read Only Memory (ROM), flash RAM, or the like; an optical transceiver 28, connected to the optical fiber 130; a user display 22, such as a display screen; a user input interface 26, which may include one or more user input devices such as a touchscreen implemented on display 22, or a keyboard, mouse, keypad, touch pad, turn-wheel, or the like; a fixed storage 23 such as a hard drive, flash storage, or the like; a removable media component 25 operable to control and receive a solid-state memory device, an optical disk, a flash drive, or the like; a network interface 29 operable to communicate with one or more remote devices via a suitable network connection; and a speaker 30 to output an audible communication to the user.

In some embodiments the user input interface 26 and the user display 22 may be combined, such as in the form of a touch screen.

The bus 21 allows data communication between the central processor 24 and one or more memory components 25, 27, which may include RAM, ROM, and other memory, as previously noted. Applications, instructions and data resident with the controller 110 are generally stored on and accessed via a computer readable storage medium.

The network interface 29 may provide a direct connection to a remote server via a wired or wireless connection. The network interface 29 may provide such connection using any suitable technique and protocol, as will be readily understood by one of skill in the art, including digital cellular telephone, WiFi, Bluetooth(R), near-field, or the like.

Figure 3:
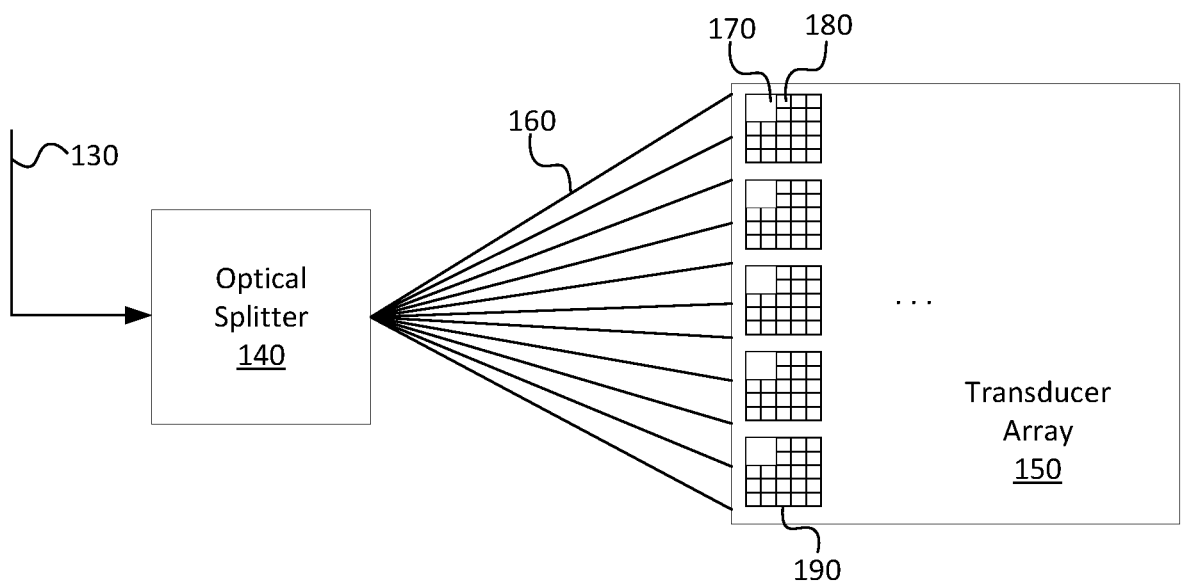
FIG. 3 shows a block diagram of a target device according to an embodiment of the disclosed subject matter.

FIG. 3 is a block diagram of an embodiment of a target device 120. The target device 120 includes a beam divider 140 and a transducer array 150. The beam divider 140 receives data from the optical fiber 130 and divides the signal into a plurality of data streams 160, which channels the data to the transducer array 150. The beam divider 140 can include one or more beam splitters for dividing a signal traveling from the controller 110 to the target device 120, and one or more beam combiners for combining signals received from the transducer array 150 to be transmitted back to the controller 110.

When the data signal is divided into data stream carriers 160 (e.g. optical fibers), each individual data stream carrier 160 transmits identical data in an identical phase. That is, as the beam divider 140 divides the optical power it does not affect the phase of the signals traveling down it. Since the speed of transmission is much faster in the optical fiber than the speed in electrical conductors, any changes in phase of the data due to differences in length of the data stream carriers 160 is minimal for the typical frequency of operation of transducers (<20 MHz). In fact, implementations of the disclosed subject matter can achieve division of data streams with essentially 0 phase shift by using data stream carriers 160 implemented with optical fibers having the same length, thereby improving the accuracy and precision of the device.

The data stream carriers 160 transmit a data stream to driver circuits 170 in the transducer array 150. In the disclosed embodiments the drivers 170 received the same data from the data stream carriers 160 at substantially the same point in time. The data can include a clock signal and instructions to individual transduction elements 180 (e.g., piezoelectric transduction element). As will be discussed further below, the instructions can include an address and a command, for example, a trigger command that causes the elements 180 to activate and emit an ultrasonic pulse.

In one embodiment, the transduction elements 180 are assigned to modules 190, where each module 190 includes a set number of elements 180 that are all controlled by a driver circuit 170. In one embodiment the modules 190 are each identical in size. In another embodiment the modules 190 differ in size. The modules 190 in FIG. 3 are depicted uniform in shape and spaced apart for the sake of clarity, however, modules 190 that are adjacent and of varying shape are within the scope of this disclosure. In a simple implementation of a module 190, the driver circuit receives an optical signal from the data stream drivers 160 and drives a plurality of level shifters that drive the elements 180. In another implementation an ASIC can receive a datagram from the data stream drivers 160 that includes information about a number of N elements and electronically activate the elements 180 based on the data in the datagram. Different configurations of driver circuits 170 in modules 190 are possible.

The disclosed embodiments utilize a global address space implemented such that each driver circuit 170 can discriminate data destined for elements 180 within that driver's module 190. Each driver circuit 170 scans the received data stream for addresses within its own space either on a per module 190 basis (e.g., ADDR:Module1_Element!7) or on a per element 180 basis (e.g. ADDR:Elementl565, ADDR:Elementl567, etc.). The addressing scheme can comprise a single 'level' for an address or multiple 'levels' as the need varies depending upon the system or application. That is, some applications may use the same hardware, however, utilize a less demanding address structure.

The arrangement of the address order in the data stream can be adjusted according to the needs of the system 100. In one embodiment the addresses are contiguous within the data stream, which can support algorithms for faster processing on the target device 120 side. In another embodiment the addresses are randomly distributed within the data stream, which can allow for faster processing on the controller 110 side in generating the data signal.

The mode of data transmission can be serial digital for relatively simple transmission of data or to reduce processing requirement. For more complex data or to increase the speed/efficiency of transmission, frequency or amplitude modulation (FM or AM) can be used. For example, in one embodiment amplitude modulation with a tracking decoder at the reception end is used to transmit the data stream.

In addition to element-by-element instructions, the controller 110 can transmit a code in the data signal that passes global instructions to the modules 190 via the data stream carriers 160. For example, the data stream carriers 160 can carry a command code for all elements 180 to activate on a next clock signal, or for all elements 180 to turn off on a next clock signal, etc. A global code can further be used to achieve synchronization among the modules 190 by instructing the modules to synchronize 190 at a given clock signal.

Regarding the clock signal, in order to provide precise performance, the clock signal must be simultaneously distributed so that all drivers 170 operate on the same frequency. The clock should be phase synchronous with the leading edge arriving at a same time on each driver circuit 170. Depending on the system capabilities, this can be achieved in different ways. In some embodiments, as described above, the data stream itself can carry clock timing data. In other embodiments a dedicated fiber cable (not shown) can be used to exclusively carry a clock timing signal. In other embodiments the clock signal can be transmitted through the same optical cables as the data signal, but use a frequency/wavelength that differs from the frequency/wavelength used to transmit the data, utilizing specific filters at the beam divider 140 to separate the clock signal from the data. The clock signal may also be distributed in the form of a frequency modulation (FM) carrier or amplitude modulation (AM) carrier, the data would be modulated appropriately atop the carrier (clock) signal. It would also be possible to modulate the data on the carrier using phase modulation or other modulation schemes such as quadrature amplitude modulation (QAM).

In some circumstances a dynamic response to a situation may require a distribution of an independent synchronization pulse, activation pulse, or clock pulse that is not embedded in the data signal. To execute a dynamic response the optical transceiver 28 can transmit the required information by transmitting a light down the fiber cable 130 in a wavelength that differs from the wavelength of light used for the data/timing signal transmission, essentially creating a secondary channel. The beam divider 140 can send a secondary signal to carry that information. In some embodiments, the addition of a frequency selective beam splitter (not shown) at each module 190 allows the separation of the two data streams with relatively little to no phase change between the modules 190. This technique can be extended to any number of signals, each with a different wavelength as required, creating multiple channels.

Certain applications can require information be transmitted back through the optical fiber 130, for example, to provide feedback for performance evaluation or when the target device 120 is an ultrasonic imager. To accomplish this, in one embodiment data from the transduction elements is collected through an ordered response to an instruction to transmit data on a per element basis (e.g., a polling algorithm executes to poll each element individually at each individual address in the transducer array). This method allows control over the rate of data being transmitted back to the controller 110 from the target device 120. In another embodiment the elements 180 can simply be configured to transmit data as it is generated in order to reduce the size, complexity and cost of control electronics.

A star combiner (not shown) in the beam divider 140 can be used to combine the data from the transduction elements into a single optical data signal. The amalgamated optical data signal can be transmitted back to the controller 110 via the optical fiber 130. If there is insufficient bandwidth for a single wavelength of light, multiple wavelengths can be used to increase the bandwidth of the channel.

Figure 4:
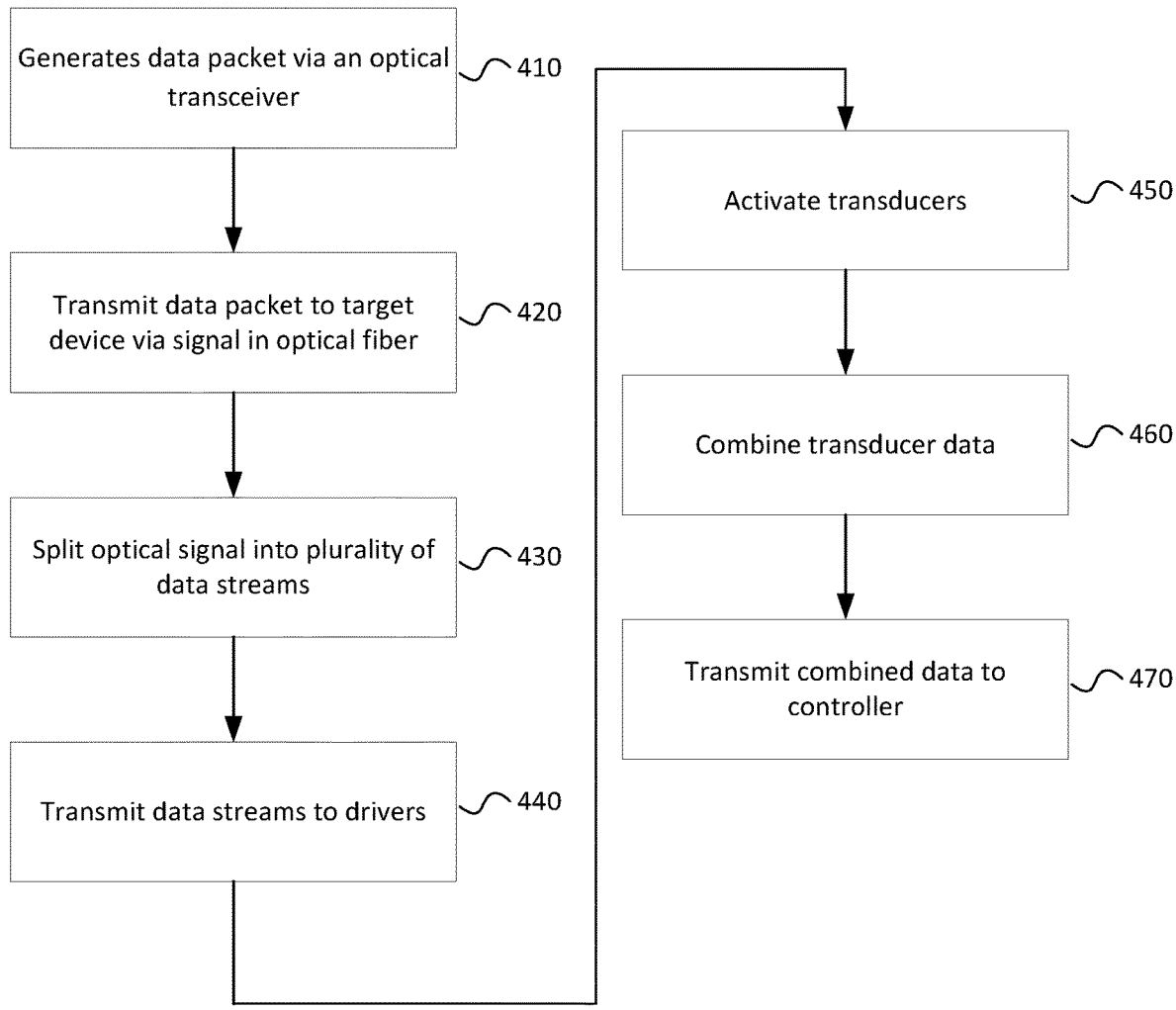
FIG. 4 shows an example flowchart of operation for an ultrasound system according to an embodiment of the disclosed subject matter.

FIG. 4 shows an example flowchart 400 of operation for the disclosed ultrasound system. As described above, the system includes a controller that controls a target device that operates a transducer array. Although the process is described as a series of operations, a person of ordinary skill in the art will recognize that other functional operations can be executed as part of the process as needed, for example, for practical implementation purposes.

At operation 410 the controller generates a data packet via an optical transceiver controlled by a processor. The data packet includes activation instructions encoded in a first wavelength. The data packet can also include a clock signal.

The clock signal can be encoded using a second wavelength different from the first wavelength.

At operation 420 the data packet is transmitted from the controller to a target device via a signal in an optical fiber, the target device having a beam divider device. At operation 430 the beam divider device splits the data signal into a plurality of data streams, each data stream carrying the data packet in an identical phase. That is, splitting the data signal occurs by dividing the data signal into two or more data streams with a zero phase shift across the divide.

At operation 440 the data streams are transmitted to drivers of the transducer array. The drivers can control individual transduction elements or control modules, where each module includes a plurality of elements. Each driver simultaneously or substantially simultaneously receives the same data in the same phase. The data can include, among other information, activation instructions for the elements, global instructions for the array, and a clock signal. Each driver scans the data received for activation instructions corresponding to addresses for one or more elements that the driver controls. The address format can be a direct element address or a module address with an element subaddress.

At operation 450 the drivers, having activation instructions and clock signal data, activates the elements. The activation instructions can include a trigger instruction having a corresponding time based on the clock signal. In total the corresponding times of the trigger instructions can vary across the array to introduce a delay and guide a wavefront created by the activation of the elements. In this manner the controller can operate the array as a phased array. In the case where the drivers receive global instructions, e.g., activate on the next clock signal, the drivers simultaneously execute the global instruction at each element in the array.

At operation 460 imaging data is received from elements in the array and combined into a return data packet. The return packet can also include additional system maintenance data, such as a measure of supply voltage to the array, current consumed by elements, modules or ASICs, temperature, etc. The return data packet can be encoded using wavelength or frequency that is different from the wavelength or frequency that was used to encode the data packet containing instructions. For example, a data packet transmitted from the controller to the target device can include activation instructions encoded in a first wavelength while a return data packet transmitted from the target device to the controller can include imaging data encoded in a second wavelength different from the first wavelength.

At operation 470 the return data packet is transmitted back to the controller via the optical fiber. The return packet can be transmitted using a third wavelength different from the first wavelength (used for original data packet) and the second wavelength (used for the clock signal).

The proposed system can be compatible with magnetic resonance imaging (MRI) systems. For MR guided high intensity focused ultrasound (HIFU) treatments the array must be capable of functioning within the magnet bore so that MR imaging can be carried out during operation. To achieve this compatibility, magnetic materials must be excluded from the design, and a configuration should be utilized that minimizes or eliminates conductor loops that carry current to prevent interference with the MR sensing.

The advantages of the disclosed embodiments are applicable to various ultrasonic imaging modalities, for example, continuous wave (CW), Doppler, B-mode, elastography, acoustic radiation force impulse (ARFI), plane wave imaging (PWI), etc., and in both high intensity focused ultrasound (HIFU) therapy and low intensity ultrasound therapy.

The disclosed system enables distribution of control data to multiple modules with zero or near zero phase shift in the data between each limb of the system. Embedding clock and data together in the same data stream allows recovery of clock signal in different modules to be phase synchronous with other modules. Furthermore, the system has the capability to distribute a separate data channel with the first data channel for timing or control, with no change in phasing between channels and data for each distribution point.

Thus, the disclosed system and methods achieve an increase in phase resolution beyond what is possible with other conventional ultrasound systems and methods. Other advantages include: I) improved closed-loop operation due to reduced delay between elements, components, and control system, 2) improved imaging and therapy within an MR system due to reduced metal or other components, 3) improved performance with arbitrary location of transduction modules and increase in overall separation, and 4) a reduction in a limit on number of phase levels that can be applied to an ultrasound system since the limiting factor is now the timing delays in the electronic circuits instead of the distribution of signals to those circuits.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

The invention claimed is:

1. A method of distributing data to a transducer array of a target device, comprising: receiving a data packet at the target device via a data signal in an optical fiber, wherein
   the data packet comprises data encoded in a first wavelength;
   splitting the data signal, using a beam divider device of the target device, into a plurality of data streams, with each of the data streams carrying the data packet in an identical phase;
   transmitting the data streams from the beam divider to drivers of the transducer array of the target device; and
   activating transduction elements of the transducer array based on the received data streams.

2. The method of claim 1, wherein the data packet includes a clock signal.

3. The method of claim 1, wherein the clock signal is encoded using a second wavelength different from the first wavelength.

4. The method of claim 2, wherein the clock signal is encoded as a carrier wave, such as FM or AM.

5. The method of claim 4, wherein the carrier wave is one of frequency modulation (FM), amplitude modulation (AM), or quadrature amplitude modulation (QAM).

6. The method of claim 1, wherein the data packet includes a global instruction that is executed by each transduction element in the transducer array.

7. The method of claim 1, further comprising:
   receiving imaging data from a plurality of transduction elements in the transducer array; combining the imaging data into a return data packet; and transmitting the return data packet back to a controller from the target device via a return signal in the optical fiber.

8. The method of claim 7, wherein the return data packet is encoded using a second wavelength different from the first wavelength.

9. The method of claim 1, wherein splitting the data signal comprises dividing the data signal into two or more data streams with a zero phase shift across the divide.

10. An ultrasonic system, comprising:
a target device comprising a transducer array and a beam divider device connected to the optical transceiver by an optical fiber, the transducer array having drivers that control transduction elements of the transducer array,
wherein the target device receives via the optical fiber in a data signal a data packet comprising data encoded in a first wavelength,
the beam divider device divides the data signal into a plurality of data streams and transmits the data streams to the drivers, and
the drivers activate the transduction elements based on the received data streams.

11. The ultrasonic system of claim 10, wherein:
the transduction elements generate imaging data, and
the optical splitting device combines the imaging data into a return data packet and transmits the return data packet to a controller via a return signal in the optical fiber.

12. The ultrasonic system of claim 10, wherein the beam divider device divides the data signal into a plurality of data streams by dividing the data signal into two or more data streams with a zero phase shift across the divide.

* * * * *